United States Patent [19]

Konstorum et al.

[11] Patent Number: 5,512,035
[45] Date of Patent: Apr. 30, 1996

[54] CABLE COMPENSATING MECHANISM FOR AN ENDOSCOPE

[75] Inventors: Gregory S. Konstorum, Stamford, Conn.; Frank D. D'Amelio, Solvang, Calif.

[73] Assignee: Circon Corporation, a Delaware corporation, Santa Barbara, Calif.

[21] Appl. No.: 330,388

[22] Filed: Oct. 27, 1994

[51] Int. Cl.$^6$ .............................. A61B 1/005; A61B 1/01
[52] U.S. Cl. ........................ 600/146; 600/148; 600/149; 604/95
[58] Field of Search ................................. 600/146, 147, 600/148, 149, 150; 138/118, DIG. 8; 403/43, 44, 45, 46, 47, 48; 604/95

[56] References Cited

U.S. PATENT DOCUMENTS

| | | | |
|---|---|---|---|
| 4,203,430 | 5/1980 | Takahashi | 600/149 |
| 4,294,233 | 10/1981 | Takahashi | 600/149 |
| 5,140,975 | 8/1992 | Krauter | 600/146 X |
| 5,388,568 | 2/1995 | Van der Heide | 600/146 |

*Primary Examiner*—Richard J. Apley
*Assistant Examiner*—Beverly M. Flanagan
*Attorney, Agent, or Firm*—Daniel J. Meaney, Jr.

[57] ABSTRACT

A cable compensating mechanism for an endoscope is shown. The endoscope has a generally elongated flexible shaft extending between a control head at a proximal end thereof and an objective assembly at the distal end thereof. The cable compensating mechanism includes an operative cable and sheath assembly which is operatively connected to the objective assembly and to the control head for deflecting the objective assembly in a selected direction.

A control mechanism is operatively connected to the operating cable and sheath assembly and is adapted to control the magnitude of tensile force developed in the operating cable in the event that deflection of the objective assembly is restrained. The control mechanism has a guide block and carriage member moveable therein. The moveable carriage member moves the operating cable and sheath assembly within the sheath. The guide block includes a first resilient member which is capable of being compressed between the guide block and the carriage member when the tensile force on the operating cable reaches a first predetermined value. The guide member includes a second resilient member to restrain movement of the carriage member when the tensile force is below said predetermined value and when said tensile force reaches at least the predetermined value, the second resilient member releases the carriage member which moves the operating cable and sheath assembly within the guide block.

13 Claims, 4 Drawing Sheets

CABLE COMPENSATING MECHANISM FOR AN ENDOSCOPE

BACKGROUND OF THE INVENTION

1. Description of the Invention

The invention relates to an endoscope having a generally elongated flexible shaft extending therebetween a control head and an objective assembly and more particularly relates to a flexible endoscope having a cable compensating mechanism for protecting an operating cable and sheath assembly against excessive tensile forces when the objective assembly at the distal end of the endoscope is restrained. The endoscope of the present invention also includes a ratchet control mechanism to inhibit reversal of motion during adjustment of the objective assembly.

2. Description of the Prior Art

Endoscopes are well-known in the art. Typically, endoscopes are optical imaging devices used for viewing objects within cavities or the internal surface of cavities. Certain endoscopes have working channels for insertion of devices to act upon or treat conditions within an operative site.

While the herein described invention has application in many fields, it has particular relevance to the medical field wherein flexible endoscopes are employed to view and treat deep and convoluted passages of the human body.

Endoscopes are also used with ultrasonic transducers mounted at the distal end. Such endoscopes are inserted through the esophagus and into the fundus of the stomach. The distal end of the endoscope is then scanned to generate an ultrasonic image of an area, such as, for example, the heart. This procedure is generally referred to as Transesophageal Electrocardiogram ("TEE").

In a typical endoscope designed for such purposes, the distal tip of the instrument is made maneuverable by employing two or more angularly spaced cables which interact mechanically with a series of vertebrated or specifically profiled rings located adjacent to the distal end of the instrument. Bending and deflection of the rings is obtained by tensioning and relaxing the cables by actuating the controls located at the proximal end of the endoscope on the control head. The means for applying tension and relaxing forces to these cables have been the subject of extensive technological effort resulting in controls such as joysticks or coaxial control wheels found on many well-known endoscopes. The object of these efforts has been to provide on the control head of the endoscope cable tensioning and relaxing means accessible and comfortable to the hands and fingers of the operator, and, consistent with holding the scope, operating all other controls, and allowing such other manipulations of the endoscope (i.e., torque, pushing and pulling) as are deemed effective for the clinical procedure for which the endoscope was designed.

One such cable compensation mechanism is disclosed in U.S. Pat. No. 4,688,555. The compensation mechanism engages the cables intermediate their ends and is effective to guard the cable against excessive loads and also to readily accommodate variations in the working length of the cables as occurs when the cable are permanently stretched.

Throughout this disclosure, it will be appreciated that the term "cable" is intended to refer to any elongate material which can be effectively utilized to operatively connect the distal end of the instrument to the control head. Thus, for purposes of the invention, wire, bands, chains and the like are considered to be equivalent to cables. The term "operating cable and sheath assembly" refers to an assembly comprising a cable located with a sheath wherein the cable moves within the sheath.

In the practice of medicine, a common form of such a device is used for inspection of the human ureter while a similarly structured device is used for inspection of the urethra and bladder. The endoscope is conventionally used in the diagnosis of tumors and other conditions in the urinary tract. The endoscopic examination involves the physician observing the urinary or vesical wall through an eyepiece in the control head of the instrument. Generally, the endoscope is provided with a source of illumination at its objective end, the end which is placed adjacent the area to be examined, and a bundle of light-transmitting fibers through which an image of the examined area is transmitted back to the eyepiece. The endoscope can further incorporate a channel which provides a washing fluid for application to the site under examination as well as a surgical tip and other features.

In TEE procedures, the distal tip of the endoscope could become internally restrained by contacting tissue or bone within the cavity during the procedure. In such event, the cable could be subject to a high tensile force or could break. If the distal tip is in a curved or deflected position and mechanically becomes fixed in the deflected position, it becomes difficult to remove the endoscope from a patient.

A factor to be considered in the construction of the endoscope for its normal medical use is its flexibility and articulation which permits the objective tip to be directed along a selected passageway such as in the esophagus or in the urinary tract. An endoscope can be made to traverse a considerable distance within the selected passageway providing that any bends in the channel have a sufficiently large radius of curvature to enable the objective assembly of the endoscope to be readily articulated to follow the course of the passageway. Care must be taken, however, to precisely guide the instrument so as not to puncture any cavity or passageway walls such as the vesical wall, especially as the device is being inserted.

Endoscopes are also used for inspecting mechanical structures requiring elongated tubular inspection devices. Typically, such endoscopes incorporate flexible fiber optics. One application is to inspect the first stage or high temperature stage of a jet engine just behind the burner in that such components are most subject to wear and deterioration. The arrangement of the jet engine's rotor and stater blades, particularly those in the high temperature state of the engine, presents a most complex geometry which has not been amenable to inspection in the past other than by first disassembling the engine.

While the state-of-the-art relating to endoscopes is relatively advanced today, there are still recurring problems which result when excessive stresses are applied to the operating cables by the hand operated control mechanism. In an extreme situations, this can result in breakage of the cable or, in a less extreme situation, to permanently stretching of the cable. In the former instance, the endoscope is rendered useless until the cable has been replaced. In a latter instance, the endoscope loses a portion of its original deflection capability, making it necessary to take up the slack of the stretched cable and to recalibrate the instrument. In both instances, it is necessary to repair the instrument to its former operating condition. This procedure, of course, results in considerable downtime thereby creating scheduling problems, possibly delaying for long periods of time critical inspection procedures which cannot be performed until the instrument has been repaired.

SUMMARY OF THE INVENTION

A new, novel and unique cable compensation mechanism for an endoscope for performing diagnostic or medical procedures is disclosed and taught by the present invention. In the preferred embodiment, the cable compensation mechanism is adapted for use with an endoscope having a generally elongated flexible shaft extending between a control head at a proximal end thereof and an objective assembly at the distal end thereof. The cable compensating mechanism comprises an operative cable and sheath assembly which extends between the central head located at the proximal end and the objective assembly located at the distal end. The operating cable is operatively connected to the objective assembly and to the control head for deflecting the objective assembly in a selected direction.

A control mechanism is operatively connected to the operating cable and sheath assembly within the control head for moving the operating cable within the sheath to deflect the objective assembly. The control mechanism is adapted to control the magnitude of tensile force developed in the operating cable in the event that deflection of the objective assembly is restrained. The control mechanism has a guide block and carriage member moveable therein wherein the moveable carriage member is operatively connected to the operating cable and sheath assembly. The guide block includes a first resilient member positioned between the moveable carriage member and the guide block. The first resilient member is capable of being compressed between the moveable carriage member and guide block when the tensile force on the operating cable reaches a first predetermined value. The guide member includes a second resilient member which is operatively connected between the operating cable and sheath assembly and the moveable carriage member and which is adjacent to the first resilient member. The second resilient member restrains movement of the carriage member when the tensile force is below the predetermined value. When the tensile force reaches at least the predetermined value, the second resilient member is responsive to absorb the tensile force in excess of the predetermined value and release the carriage member. The carriage member moves the sheath within the guide block to prevent the tensile force from being applied to and impairing the operating cable and sheath assembly.

Each of the known prior art devices and methods have certain disadvantages.

In certain of the known endoscope structures, the control head relies on the mechanical strength of the guide block to resist the tensile force which is generated in the operating cable when the distal end is restrained and the operator continues to rotate the deflection wheel in an attempt to cause the distal tip to deflect. If the tensile force exceeds the tensile strength of the cable, the cable, due to its elasticity, will stretch and become permanently deformed.

If the tensile force reaches a sufficiently high force value, the operating cable could be broken.

Therefore, the problems associated with the prior art devices are that the mechanically rigidity of the guide block is relied upon to accommodate and absorb the tensile forces generated within the cables. If the forces become sufficiently large the guide block can be physically deformed by the tensile forces. In the absence of a cable compensation mechanism, permanent cable deformation clearly occurs.

The cable compensation mechanism disclosed in U.S. Pat. No. 4,688,555 provides a coil spring to guard against excessive cable loads, but the operating cables experience permanent deformation. Thus, the cable compensation mechanism in U.S. Pat. No. 4,688,555 functions to accommodate variations in the working length of the cable device to permanent deformation. However, permanent deformation of the cables can occur.

The cable compensation mechanism of the present invention overcomes several of the problems associated with the prior art mechanism. The preferred embodiment of the present invention is the form of a Transesophageal Electrocardiogram transducer or probe ("TEE Probe") wherein the objective assembly has an ultrasonic transducer mounted therein. However, the principles of the present invention also apply to an endoscope having a flexible lens system mounted therein with an objective lens located at the distal end thereof.

One advantage of the present invention is that the cable compensating mechanism absorbs the tensile forces developed within the operating cable when deflection of the distal end is restrained thereby preventing stretching and or breakage of the operating cable.

Another advantage of the present invention is that the cable compensation mechanism includes a first resilient member, which in the preferred embodiment is a coil spring which absorbs a tensile force which is less than a predetermined value.

Another advantage of the present invention is that the cable compensation mechanism includes a second resilient means, which in the preferred embodiment is a pair of elongated flat springs, which absorb the cable sheath compressive force above a predetermined value.

Another advantage of the present invention is that the guide block includes a carriage member which is operatively connected to the operating cable and sheath assembly. When the tension force reaches the predetermined value, the elongated leaf springs absorb the excessive compressive force by becoming bowed or buckled to release the carriage member. The carriage member moves both the cable and sheath of the operating cable and sheath assembly with the guide block to insure that the tensile force does not impair the operating cable. Thus, the cable compensation mechanism insures that the operating cable is not subject to permanent deformation or possible cable breakage.

Another advantage of the present invention is that the elongated leaf spring structure can be used to absorb tensile force for one to four deflection modes depending on the application.

Another advantage of the present invention is that the control mechanism can include means for activating a ratchet mechanism to insure that a reversal of deflection does not occur during usage.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figures 1, 2, 3:
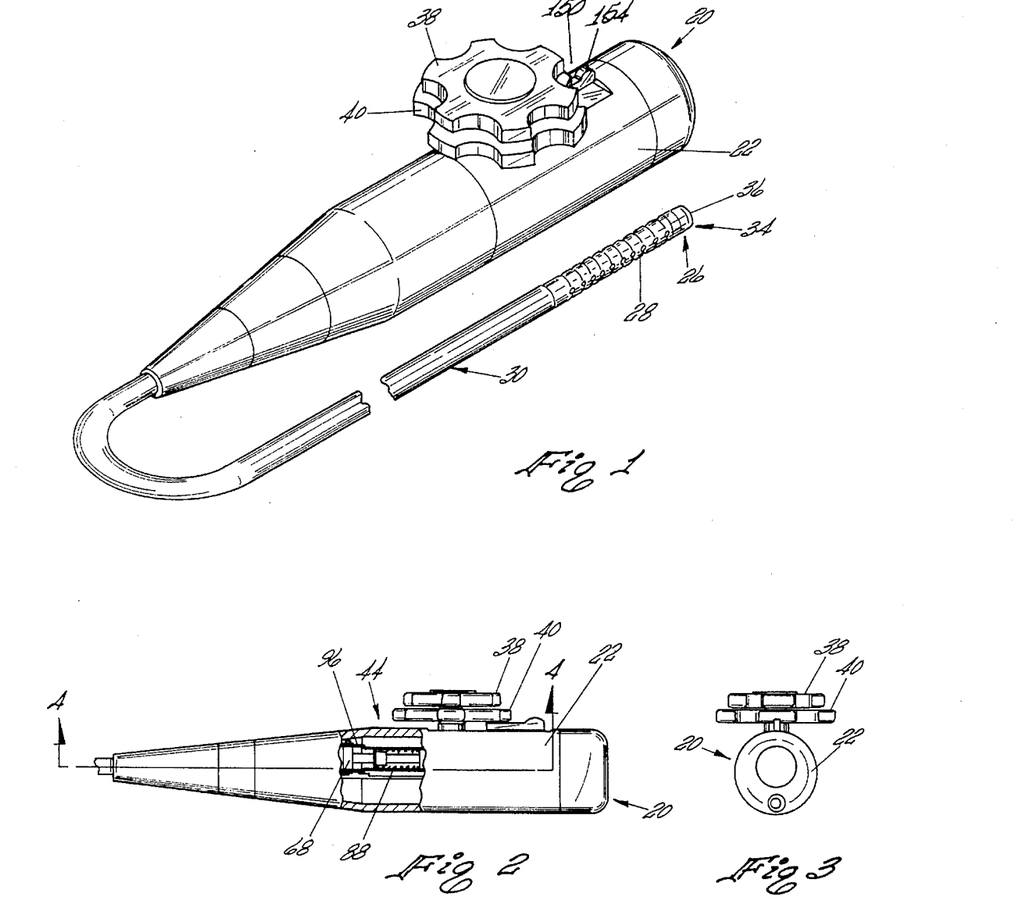
FIG. 1 is a top, front and left side perspective view of a flexible endoscope having a cable compensation mechanism and ratchet control mechanism subject of the present invention.
FIG. 2 is a partial cross-sectional, front plan view of a control head of a flexible endoscope incorporating the cable compensation and ratchet control mechanism subject of the present invention.
FIG. 3 is a right side elevational view of the flexible endoscope illustrated in FIG. 2.

FIG. 1 illustrates a flexible endoscope, when generally as 20, having control head 22 at the proximal end thereof and objective assembly 26 located at the distal end thereof. A generally elongated flexible shaft, shown generally as 30, extends between the control head 22 and the objective assembly 26. A scanning element 34, such as a transducer or objective lens, may be located at the distal end 26.

In the preferred embodiment, the objective assembly includes a bending section 28 which is in the form of a series of vertebrated or specifically profiled rings, which are well known in the art, located adjacent to the distal end of the instrument. The preferred embodiment has an ultrasonic transducer 36 located at the distal end of the objective assembly. The ultrasonic transducer is the scanning element of the TEE Probe which is capable of producing an ultrasonic image of an operative site.

Figure 7A:
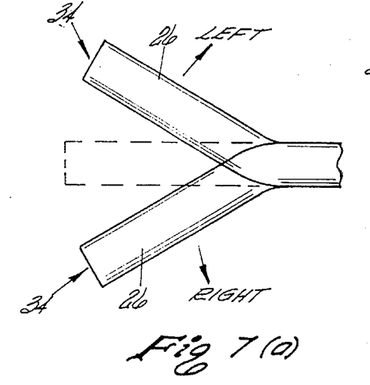
FIG. 7(a) is a partial representation of the left and right deflection of the objective assembly in response to the rotation of the top deflective control knob.

The flexible endoscope 20 has a pair of coaxially aligned disc shaped deflection control knobs 38 and 40. Deflection control knob 38 is the first knob and controls the left and right deflection of the objective assembly 26 which is depicted by FIG. 7(a).

Figure 7B:
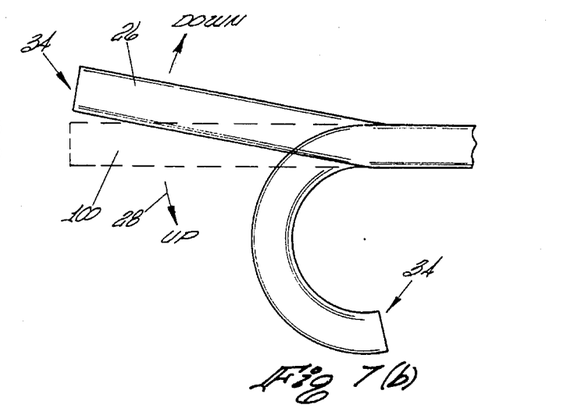
FIG. 7(b) is a pictorial representation of the up and down deflection of the objective assembly wherein the restrained objective assembly is shown by dashed lines.

Deflection control knob 40 is the second knob and controls the up and down deflection of the objective assembly 26 which is depicted in FIG. 7(b).

An operating cable and sheath assembly extends between the control head 22 and the objective assembly 26 located at the distal end. The operating cable is operatively connected to the objective assembly 26 for moving the operating cable within the sheath and for deflecting the objective assembly in a selected direction. The objective assembly 26 includes the controlled bending section 28.

In the preferred embodiment illustrated in FIG. 1, each deflection control knobs 38 and 40 is operatively connected to its associated operating cable and sheath assembly. The first deflection control knob 38 deflects the objective assembly left and right over a total of 60° arc. The second deflection control knob deflects the objective assembly up and down over a total of 110° arc [as shown by the arrow 28 on FIG. 7(b)], with the major deflection in the up direction causing the objective assembly to be extensively curved as shown by FIG. 7(b).

The deflection control knobs 38 and 40 enable the user to essentially scan the distal end of the objective assembly 26 such that the scanned distal end 34 can scan a diagnostic site. In the preferred embodiment, once the TEE Probe is inserted into the esophagus or stomach of the patient, the ultrasonic transducer 36 can be selectively scanned over the heart to generate an ultrasonic image which is used for diagnostic purposes.

In the alternative, a lens system can be located with the flexible shaft 30 and an objective lens can be located at the distal end 34. Typically, a fiber optic light guide is located adjacent the lens system to illuminate the operative site enabling an optical image to be transmitted from the distal end.

Figure 4:
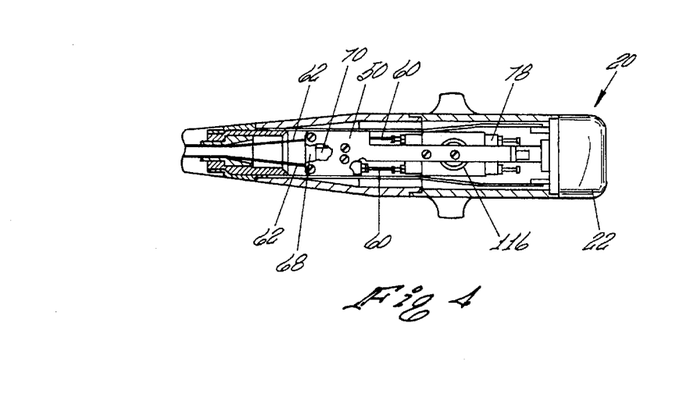
FIG. 4 is a bottom plan view of the cable compensation mechanism and ratchet control mechanism located in the control head of the flexible endoscope taken along section lines 4—4 of FIG. 2.
Figure 6:
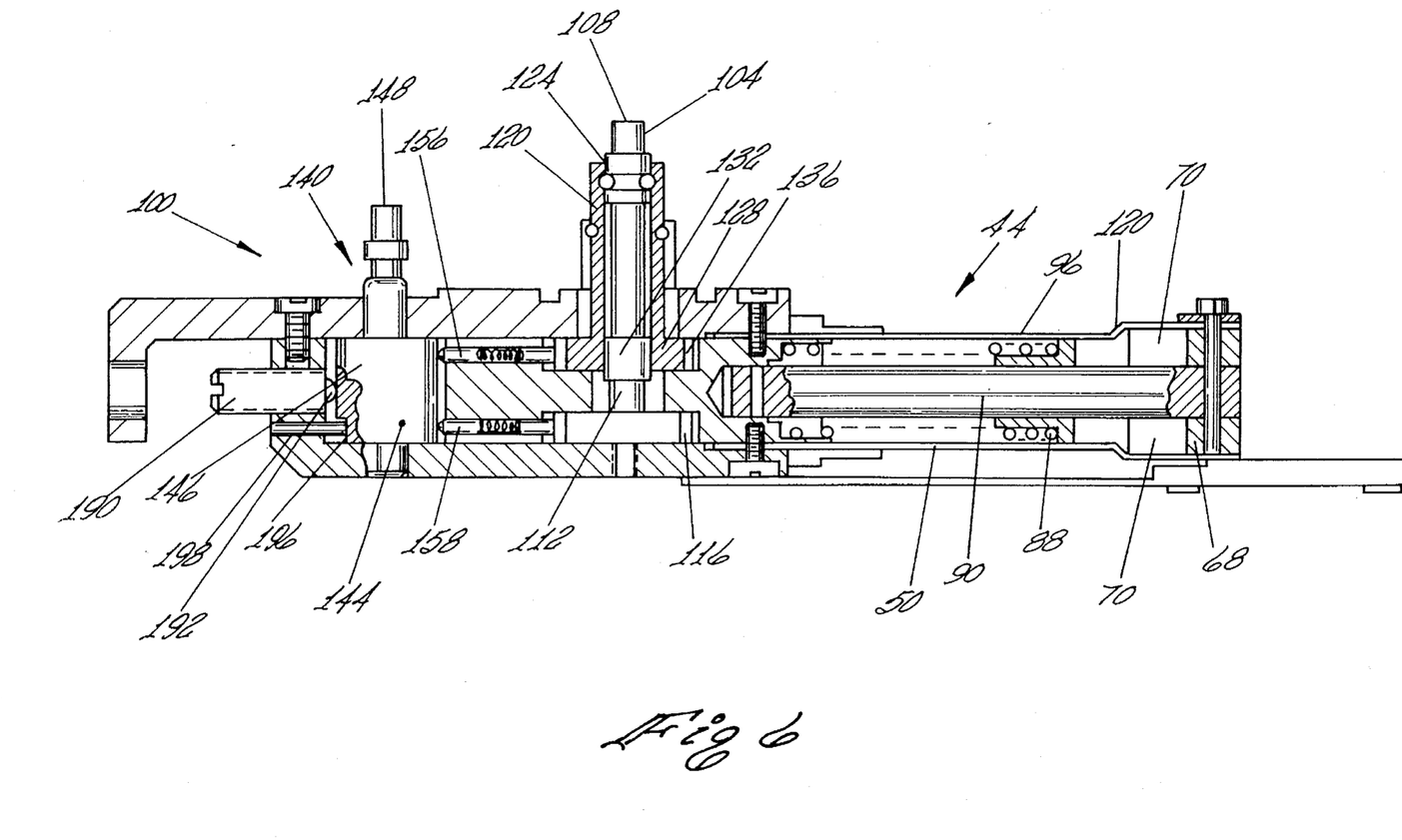
FIG. 6 is a partial cross-sectional front view of the cable compensation mechanism and ratchet control mechanism.

FIGS. 2, 4 and 6 show the details of the cable compensation mechanism and the ratchet control mechanism.

The cable compensation mechanism is shown generally by 44. The control head 22 encloses the operative cable and sheath assemblies for both deflection control knobs 38 and 40. The first deflection control knob 38 controls the operating cable 60 which moves within its associated sheath. The second deflection control knob 40 controls operating cable 60 which moves with sheath 62. In the preferred embodiment, the operating cable 60 and sheath 62 assembly controls the up and down motion of the objective assembly 26.

In the preferred embodiment, the cable compensation mechanism 44 is fabricated to be responsive only to the condition that the objective assembly 26 is restrained in the relatively straight position showed by dashed line 100 in FIG. 7(b).

However, the structure of the cable compensation mechanism may permit responding to the objective assembly 26 in all four modes, left, right, up and down. The preferred embodiment is specifically designed for the maximum 60° left and right and 140° up and down.

In the preferred embodiment, the restrained condition would occur if the user rotates the second deflection control knob and the distal end of the objective assembly in the up mode is urged against tissue or bone preventing the objective assembly from moving. Thus, the user, by rotating the deflection control knob 40 cause a tensile force to be applied to its associated operative cable 60 which, since the cable sheath is rigidly held in position by the control head, develops a differential force between the operating cable 60 and sheath 62.

A similar condition could occur for the down, left or right mode and the structure of the cable compensation mechanism can likewise include a structure enabling compensation for all modes.

In FIGS. 2, 4 and 6 the control head 22 enables the control mechanism 44 which includes a guide block 68 which includes a carriage member 70 which is moveable therein. The carriage member 70 is operatively connected to the sheath 62 [see FIGS. 8(a), 8(b) and 8(c) for details] and includes an opening 94 which permits the cable 60 to pass therethrough and is terminated in a moveable cable termination member as shown by 78 in the opposite end of the guide block 68. If compensation is desired for one or more of the other modes, each quadrant of the carriage member is rendered separate and distinct quadrants and can be used to compensate for restraint in one or more of the left, right, up and down modes.

In the preferred embodiment, the position of the carriage member 70 viewed from the bottom is one-half of the carriage member 70 wherein each of the two quadrants thereof are separate. FIG. 6 shows the top half of the carriage member 70. The top half is divided into two separate quadrants and all quadrants can be operative when the tensile force exceeds the predetermined values.

If compensation is desired for one or more of the other modes, each quadrant of the carriage member 70 is rendered a separate and distinct quadrant and can be used to compensate for restraint in one or more of the left, right, up and down modes. The compensation is independent of angle of deflection and depends only on cable tension.

The guide block 68 includes a first resilient member which, in the preferred embodiment, is a coil spring 88, which has a guide shaft 90 coaxially aligned therewith as the tensile force in the operating cable 60 increases, the cable termination member 78 (shown in FIG. 2) is urged against and compresses coil spring 88. Thus, in the absence of a tensile force, coil spring 88 is in a pre-compressed state and when a tensile force is developed, the coil spring then becomes more compressed and is, therefore, in a compressed state. The embodiment illustrated in FIGS. 2 and 6 directs approximately 50% of the maximum value of the tensile force in coil spring 88. Thus the predetermined value of tensile force absorbed by the coil spring 88 is in the range of about 6 pounds to about 8 pounds, with about 7 pounds being preferred in this preferred embodiment.

FIG. 3 illustrates the first deflection control knob 38 and second deflection control knob 40 are located in the control head 22 at the proximal end of the endoscope 20.

In FIG. 4, the guide block 68 has a second resilient member, which in the preferred embodiment, is one set of a pair of spaced co-planar, elongated flat springs 50. A second set of a similar pair of leaf springs 96 are located on the opposite side of the guide block 68 as shown in FIG. 6. The elongated flat springs 96 are connected to between the cable termination member 78 and the guide block 68. Therefore, there are four separate leaf springs in this embodiment.

In the preferred embodiment, as the tensile force exceeds the predetermined value established by the selected characteristics of the coil spring 88, the force is then absorbed by the elongated flat spring 96. As the tensile force increases, the flat springs 96 bend permitting the carriage member 70 which is fixedly attached to sheath 62 to move or slide within the guide block 68. Thus, the cable 60 and sheath 62 are moved which relieves the tensile force from the operating cable and sheath assembly. The flat spring 96 is in an unflexed state when the tensile force is below the predetermined value and when the tensile force is in excess of the predetermined value, the bending or buckling of the leaf spring is referred to herein as the flexed state.

When the cause of the restraint condition is removed, the coil spring 88 causes the objective assembly 26 to be returned to its undeflected position.

Also, FIG. 6 shows in detail the ratchet control mechanism shown generally as 100.

The ratchet control mechanism 100 has an inner shaft 104 has an end which terminates in a driving end 108 and a second end 112 which is operatively connected to a first spur gear 116. The first driving end 108 is operatively connected to the first deflection control knob 38 shown in FIGS. 1, 3 and 5.

The ratchet control mechanism 100 also includes an outer shaft 120 having an opening 124 extending therethrough and which encloses the inner shaft 104. The outer shaft 120 has one end thereof which terminates in a second driving member 128 and has a second end 132 which is operatively connected to a second spur gear 136.

The outer shaft 120 rotatably supports the inner shaft 104 in a structure wherein the first spur gear 116 on the second end 112 is in a spaced opposed relationship from the second spur gear 136 on the second end 132 of the outer shaft 120. Thus, the first spur gear 116 is closer to the driving ends 108 and 128 and the second spur gear 136 is positioned in an opposite spaced relationship to spur gear 116.

The ratchet control mechanism 100 further includes a means defining a ratchet mechanism shown generally as 140. The ratchet mechanism 140 includes a rotatable ratchet shaft or rotatable ratchet member 144 having an outer cam surface 146. The outer cam surface 146 defines at selected locations thereon a first indentation 170 and a second indentation 172 [shown in FIGS. 9 and 10(b)]. The ratchet member 144 is positioned substantially perpendicular to and spaced from the first spur gear 116 and the second spur gear 136.

The ratchet control mechanism 100 further includes a pair of resilient activation members such as, for example, spring loaded pin members 156 and 158. Each of the spring loaded pin members 156 and 158 have a compressed state and uncompressed state. The spring loaded pin members 156 and 158 are positioned in the space between the ratchet member 144 and the first spur gear 116 and the second spur gear 136.

The structural details of the ratchet control mechanism will be discussed in greater detail in FIGS. 9, 10(a), 10(b), 11(a), 11(b), 12(a) and 12(b).

Referring again to FIG. 4, the bottom plan view of the control head 22 of the endoscope 20 shows the pair of spaced, elongated co-planar leaf springs 50 in an uncompressed or unflexed state. This is the same state for leaf springs 96 shown in FIG. 6. The guide block 68 supports the cable termination member 78 enabling the tensile force to be transferred to the coil spring 88 and to one of the leaf springs 96 only.

Figure 5:
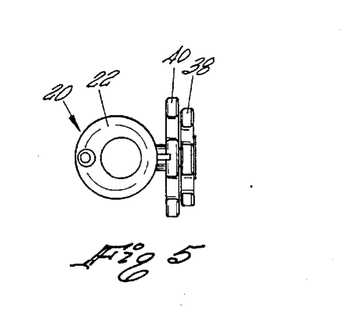
FIG. 5 is a right side elevational view of the control head of the flexible endoscope of FIG. 4.

FIG. 5 illustrates the relationship between the first deflection control knob 38 and the second spur gear 116 shown in FIGS. 4 and 6.

In FIG. 6, the ratchet member 144 has three index indentations in the form of 90° counter bores formed in the outer cam surface 146. This is covered in greater detail in FIGS. 9, 19(a), 10(b), 11(a), 11(b), 12(a) and 12(b) as discussed below.

FIG. 7(a) is a pictorial representation of the objective assembly 26 in the left mode and right mode wherein the aggregate deflection between the left and right mode positions is about 60°.

FIG. 7(b) is a pictorial representation of the objective assembly 26 in the down mode and maximum up mode wherein the aggregate deflection between the up mode and down mode positions is about 140°. The plane of deflection of the left and right mode is substantially perpendicular to the plane of deflection of the up and down mode. Thus, by controlling the relative direction of the distal end 34 in left and right mode with the first deflection control knob 38 and the up and down mode with the second deflection control knob 40, the distal end 34 of the objective assembly 26 can be positioned and/or scanned within the arc circumscribed by the congruent arc of deflection of both modes.

Dashed lines 100 depict the restrained position of the objective assembly 26 in the up mode. In the event that the objective assembly 26 encounters an obstacle that restricts its movement to the position shown by dashed line 100, a large tensile force is developed within the operating cable 60 due to the force exerted on the cable 60 by the second deflection knob 40. A similar action occurs if the deflective mechanism is in the deflected position and it is restrained in being moved back to the undeflected position.

Thus, the cable compensation mechanism structure absorbs the large tensile forces that are developed during this stressed condition.

Figure 8A:
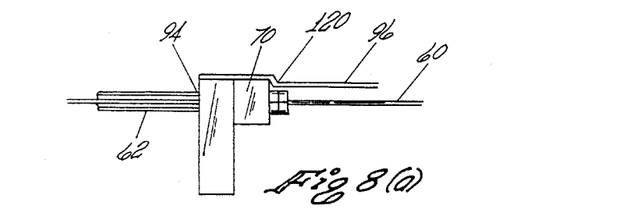
FIGS. 8(a), 8(b) and 8(c) illustrate pictorially the response of an elongated, flat spring and carriage member showing the position of the element when: (i) the tensile force is below a predetermined value and the stop member restrains the carriage member; (ii) the tensile force begins to exceed the predetermined value to start bending of the elongated spring; and (iii) the tensile force reaches a level to bend the flat spring causing the stop member to release the carriage member, respectively.
Figure 8B:
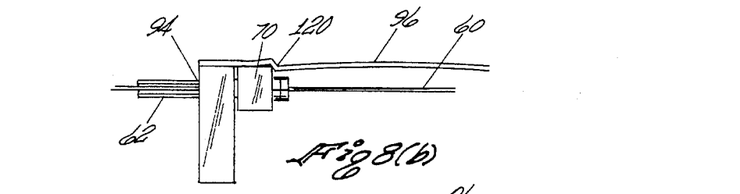
Figures 8C, 9:
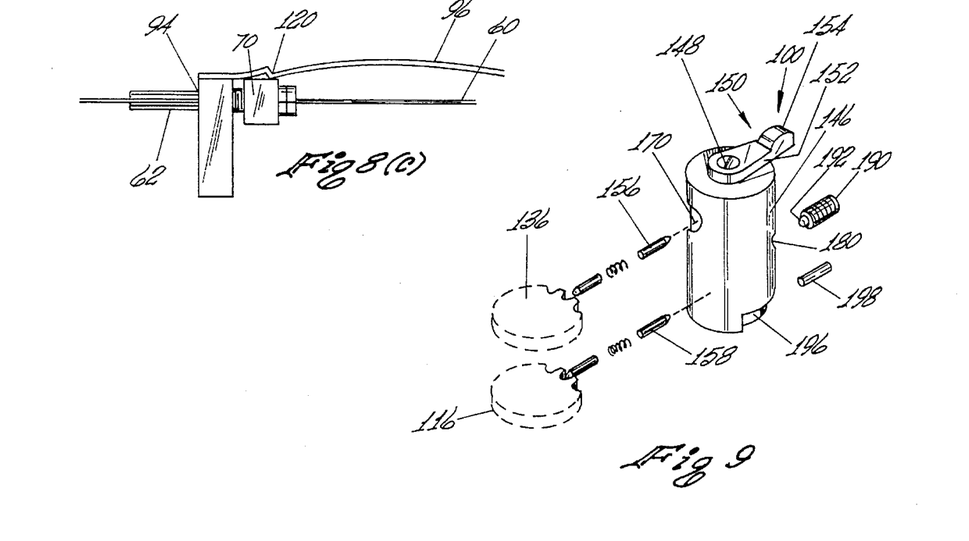
FIG. 9 is a top, front and left side perspective view of the ratchet control mechanism.

FIGS. 8(a), 8(b) and 8(c) depict the sequence of how the tensile force above the predetermined value is transferred to the second resilient means, which in the preferred embodiment, is one of the two leaf springs 96. Again, the preferred embodiment is to compensate for restrained deflection in all four modes. However, as discussed herein, compensation can be restricted only to the up mode as described herein.

In FIG. 8(a), the leaf spring 96 is shown to have a stop member 120 formed therein which engages and restrains movement of the carriage member 70 when the leaf spring 96 is flat, or in its uncompressed or unflexed state. The carriage member 70 is attached to sheath 62 as shown in FIG. 8(a). The operating cable 60 passes through opening 94 and the carriage member 70 and extends to the termination member 78.

FIG. 8(b) illustrates that as the tensile force exceeds the predetermined value, the elongated spring 96 begins to bend lifting step member 120 away from the carriage member 70.

FIG. 8(c) illustrates that when the tensile force reaches the maximum value, the leaf spring 96 is substantially deflected, in the flexed state, thereby absorbing the excess tensile force. The stop member 120 is lifted away from the associated quadrant of the carriage member 70 releasing the same. The so released quadrant carriage member 70 then moves forward in the guide block 68 towards to termination member 78 and pulls the sheath 62 therewith to prevent the tensile force from being applied to and impair the operating cable 60 and the sheath 62 assembly.

FIG. 9 illustrates the ratchet control mechanism 100 in greater detail.

The ratchet shaft 144 has an outer cam surface 146 which is treated to have certain depressed sections formed thereon.

Figure 10A:
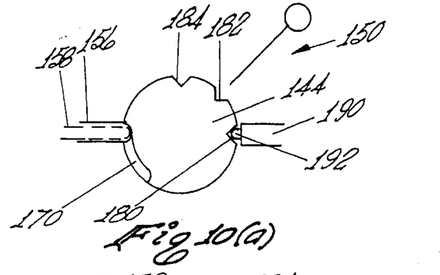
FIGS. 10(a) and 10(b) illustrate the relationship between the ratchet shaft and spring loaded pin members when the ratchet is disabled and the location of the ends of the spring loaded members is the first and second indentation located in the outer cam surface of the ratchet shaft.
Figure 10B:
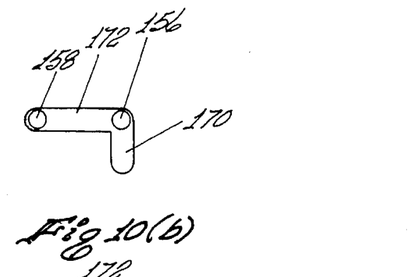

A first indentation 170 and a second indentation 172 [shown in FIG. 10(b)] are adapted to co-act with the spring loaded pin members 156 and 158. Specifically, the first spring loaded pin member 156 cooperates with the first indentation 170 and the second spring loaded pin member 158 cooperates with the second indentation 172 which is on the outer cam surface 146 but which is out of view.

The first spring loaded pin member 156 is associated with the up and down modes and cooperates with the second spur gear 136. The second spring loaded pin member 158 is associated with the left and right modes and cooperates with the first spur gear 116.

The position of the ratchet shaft 144 as shown in FIG. 9 corresponds with the diagrammatic position shown in FIG. 11(a) and 11(b) which is discussed hereinafter.

In the position depicted by FIG. 9, the first spring loaded pin member 156 has one end in the first indentation 170 which keeps the spring in an uncompressed state holding the other end of the first spring member 156 out of engagement with the second spur gear 136. Thus, the first spring load pin member 156 is out of ratchet engagement with the second spur gear 136.

The second spring loaded pin member 158 has its one end out of the second indentation 172 and in sliding engagement with the outer cam surface 146. Thus, the second spring loaded pin member 158 is in the compressed state and its other end is urged into the teeth on the first spur gear 116 forming a ratchet engagement. The ratchet engagement inhibits reversal of motion of the spur gear 116.

The ratchet shaft 144 has an elongated shaft 148 extending therefrom which is operatively connected to an elongated lever 150 at end 152. End 154 of lever 150 is in the form of a raised ridge which accommodates the end of the users fingers for adjusting the elongated lever 150 between the various ratchet index positions.

The outer cam surface 146 also has three 90° counter bores, of which 180 is typical, to cooperate with a spring loaded mechanism 190 having a plunger 192 which cooperates with the counter bore. This will be discussed in greater detail in connection with FIGS. 10(a), 11(a) and 12(a).

The end of the outer cam surface 146 opposite to the elongated shaft 148 has a slot 196 formed thereon to receive a locking pin 198. The slot 196 and locking pin 198 relationship is shown in detail in FIG. 6.

Referring now to FIG. 10(a), the ratchet member 144 cooperates with a spring load member 190 having a plunger 192 which cooperates with three 90° counter bores 180, 182 and 184, respectively. The counter bores form three index positions of: (i) no ratchet engagement; (ii) first deflection control knob 38 only in ratchet engagement; and (iii) both first deflection control knob 38 and second deflection control knob 40 in ratchet engagement.

FIGS. 10(a) and 10(b) illustrate pictorially no ratchet engagement. Both ends of each of the spring loaded pin members 156 (top) and 158 (bottom) are located within its associated indentations 170 and 172 causing the spring loaded pin members 156 and 158 to be in an uncompressed state. The location of the elongated lever 150 places 90° counter bore 180 into engagement with plunger 192 of the spring loaded mechanism 190.

FIG. 10(b) illustrate pictorially the ends of each of the first spring loaded pin member 156 and the second spring loaded pin member 158 in the first indentation 170 and second indentation 172, respectively.

Figure 11A:
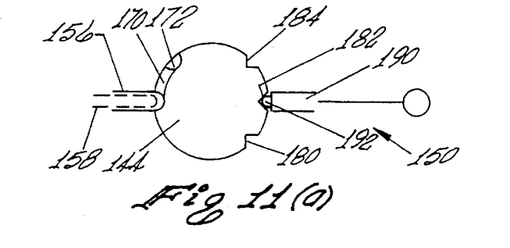
FIGS. 11(a) and 11(b) illustrate the relationship between the ratchet shaft and spring loaded pin members, when the second deflection control knob has the ratchet mechanism engaged and the location of the end of the spring loaded member therefor in engagement with the cam outer surface to urge the spring loaded pin into ratchet engagement with the second spur gear.

FIG. 11(a) illustrates pictorially that the elongated lever 150 was moved to rotate the ratchet shaft 144 an angle of 45° to cause ratchet engagement for the first spur gear 116. The spring loaded mechanism 190 moves plunger 192 into counter bore 182. Rotation of the ratchet shaft 144 causes one end of the second spring loaded member 156 to engage the outer cam surface 146 compressing the second spring loaded pin member 158 urging the other end thereof into the first spur gear 116. This is depicted in FIG. 9.

Figure 11B:
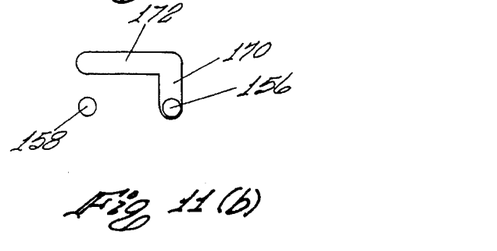

FIG. 11(b) depicts pictorially the location of the second spring loaded pin member 158 on the outer cam surface 146 and the first spring loaded member 156 in the first indentation 170.

Figure 12A:
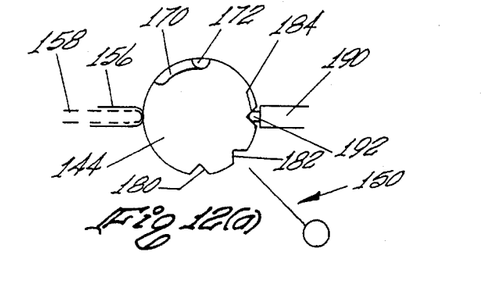
FIGS. 12(a) and 12(b) illustrate the relationship between the ratchet shaft and spring loaded pin members when both the first and second deflection control knob has the ratchet mechanism engaged and the location of the ends of the spring loaded members therefor in engagement with the cam outer surface to urge the spring loaded pins into ratchet engagement with the first and second spur gear, respectively.

FIG. 12(a) depicts pictorially that the elongated lever 150 has been rotated which rotates the ratchet shaft 144 an additional 45°. This causes the spring loaded mechanism 190 to urge plunger 192 into counter bore 184.

The rotation of the ratchet shaft 144 causes both one ends of each of the spring loaded pin members 156 and 158 to engage the outer cam surface 146.

This causes the spring loaded pin members 156 and 158 to be compressed urging the appropriate ends thereof into the teeth of the associated spur gears 136 and 116, respectively.

Figure 12B:
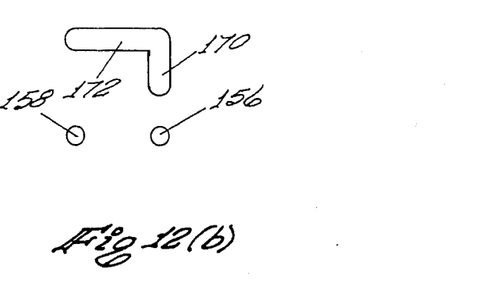

FIG. 12(b) pictorially represents that each one end of each of the spring loaded pin member 156 and 158 are outside of the indentations 170 and 172 and are in engagement with the outer cam surface 146. This results in both deflection control knobs 38 and 40 being in ratchet engagement.

Figure 13A:
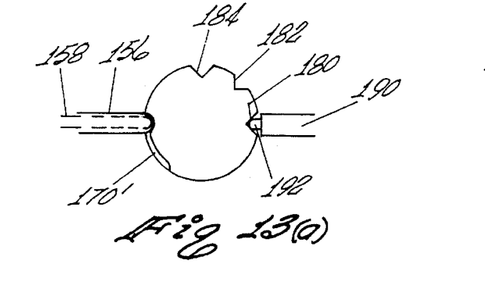
FIG. 13(a) illustrates pictorially a light ratchet engagement embodiment.
Figure 13B:
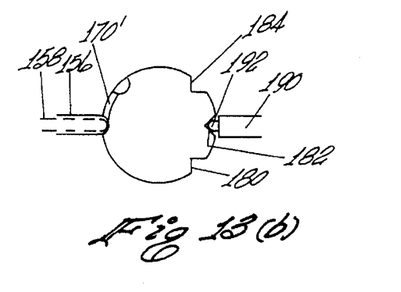
FIG. 13(b) illustrates pictorially a medium ratchet position.
Figure 13C:
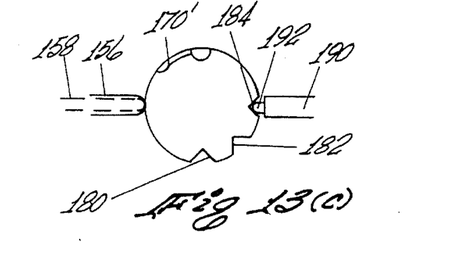
FIG. 13(c) illustrates pictorially a continuous, full ratchet engagement.

FIGS. 13(a), 13(b) and 13(c) illustrate the ratchet shaft 144 wherein the indentation 170 varies in depth and the variable indentation is shown by 170. This arrangement provides for light, medium and heavy ratcheting.

In the preferred embodiment, the diameter of the spur gears are equal. Therefore, the length of the spring loaded pin members are equal. However, it is envisioned that the spur gear and spring loaded pin member could be of different sizes and be appropriately dimensioned. Also, the operating cable and sheath assemblies are shown as separate individual segments. However, a continuous assembly could be used in lieu of separate segments.

The preferred embodiment shown and described herein is directed for use in a medical procedure, preferably a TEE procedure. However, this is an exemplary use and it is envisioned that the principle and teaching herein could be adapted for other procedures as described herein. These procedures include other medical procedures, such as urological procedures, or industrial procedures.

What is claimed is:

1. A cable compensating mechanism comprising: an endoscope having a generally elongated flexible shaft extending between a control head at a proximal end thereof and an objective assembly at the distal end thereof, wherein said cable compensating mechanism further comprises:

an operative cable and sheath assembly extending between the control head located at said proximal end and the objective assembly located at said distal end, said operating cable being operatively connected to the objective assembly and to said control head for moving the operative cable within the sheath and deflecting the objective assembly in a selected direction;

a control mechanism operatively connected to said operating cable and sheath assembly for controlling the magnitude of tensile force developed in said operating cable in the event that deflection of the objective assembly is restrained, said control mechanism having a guide block and carriage member moveable therein wherein said moveable carriage member is operatively connected to said operating cable and sheath assembly for actuating movement of said operating cable within said sheath, said guide block including a first resilient member positioned between said moveable carriage member and said guide block wherein said first resilient member is capable of being compressed therebetween when the tensile force on the operating cable reaches a first predetermined value, said guide member including a second resilient member operatively connected between said operating cable and sheath assembly and said moveable carriage member adjacent said first resilient member to restrain movement of the carriage member when the tensile force is below said predetermined value and when said tensile force reaches at least said predetermined value, said second resilient member is responsive to absorb the tensile force in excess of said predetermined value and release the carriage member which moves the operating cable and sheath assembly within said guide block to prevent the tensile force from being applied to and impairing said operating cable and sheath assembly.

2. The cable compensating mechanism of claim 1 wherein said first resilient member is a coil spring.

3. The cable compensating mechanism of claim 2 wherein said resilient member is a leaf spring.

4. The cable compensating mechanism of claim 3 wherein said leaf spring comprises a pair of spaced, co-planar, elongated flat springs.

5. The cable compensating mechanism of claim 4 wherein each of the elongated flat springs have one end thereof operatively connected to the guide block and its other end operatively connected to a cable termination member with one end of each of the elongated flat springs being located adjacent the carriage member and wherein said one end of each flat spring has a depressed shoulder section defining a stop member which engages and restricts the movement of the carriage member within the guide block when said flat spring is in an unflexed state and which releases and permits movement of the carriage member together with the operating cable and sheath assembly within the guide block when said flat spring is in a flexed state.

6. The cable compensating mechanism of claim 5 wherein the control head includes a first adjusting member and second adjusting member wherein said first adjusting member moves said objective assembly in a first direction over a first selected angle and second adjusting member which moves the objective assembly in a second direction over a second selected angle, said first adjusting means having a first operating cable and sheath assembly operatively connected thereto and said second adjusting means having a second operating cable and sheath assembly operatively connected thereto, said cable compensating mechanism being responsive to said second cable and sheath assembly tensile force to actuate movement of said carriage member in response to a tensile force in excess of said predetermined value.

7. The cable compensating mechanism of claim 6 wherein said first selected angle is an acute angle and the second selected angle is an obtuse angle.

8. The cable compensating mechanism of claim 7 wherein said acute angle is about 60° and said obtuse angle is about 110°.

9. The cable compensating mechanism of claim 1 wherein the control head includes means for moving the objective assembly in a first plane between a left mode and right mode and means for moving the objective assembly in a second plane which is perpendicular to the first plane between an up mode and a down mode.

10. The cable compensating mechanism of claim 9 wherein said second resilient member is a pair of leaf springs and the carriage member has one quadrant section that relieves the tensile force when the objective assembly is restrained in the up mode.

11. The cable compensating mechanism of claim 9 wherein said second resilient member comprises two sets of leaf springs wherein each set includes a pair of leaf springs and the carriage member has four quadrant sections that relieve tensile force when the objective assembly is restrained on any one of the up mode, down mode, left mode or right mode.

12. The cable compensating mechanism of claim 1 wherein the operating cable in the operating cable and sheath assembly are individual segments extending from the cable termination member to the objective assembly.

13. The cable compensating mechanism of claim 1 wherein an ultrasonic transducer is located in the distal end of the objective assembly and wherein said ultrasonic transducer can be scanned over an arc congruent with the arc of the first selected angle and the arc of the second selected angle.

* * * * *